US009580763B2

(12) United States Patent
Wallberg et al.

(10) Patent No.: US 9,580,763 B2
(45) Date of Patent: Feb. 28, 2017

(54) IMAGE ANALYSIS BASED PROCESS CONTROL OF PROCESSES FOR PRODUCTION OF SUGAR FROM LIGNOCELLULOSIC BIOMASS

(71) Applicant: SEKAB E-TECHNOLOGY AB, Ornskoldsvik (SE)

(72) Inventors: Marie-Louise Wallberg, Domsjo (SE); Elias Sundvall, Domsjo (SE)

(73) Assignee: SEKAB E-Technology AB, Örnsköldsvik (SE)

( * ) Notice: Subject to any disclaimer, the term of this patent is extended or adjusted under 35 U.S.C. 154(b) by 52 days.

(21) Appl. No.: 14/759,108

(22) PCT Filed: Jan. 21, 2014

(86) PCT No.: PCT/EP2014/051150
§ 371 (c)(1),
(2) Date: Jul. 2, 2015

(87) PCT Pub. No.: WO2014/114647
PCT Pub. Date: Jul. 31, 2014

(65) Prior Publication Data
US 2015/0361512 A1    Dec. 17, 2015

(30) Foreign Application Priority Data

Jan. 23, 2013    (EP) ..................... 13152377

(51) Int. Cl.
*G06K 9/00*    (2006.01)
*C12Q 3/00*    (2006.01)
(Continued)

(52) U.S. Cl.
CPC ............... *C12Q 3/00* (2013.01); *C12M 21/18* (2013.01); *C12M 41/32* (2013.01); *C12M 41/36* (2013.01);
(Continued)

(58) Field of Classification Search
CPC .............. C12Q 3/00; C12P 7/10; C12P 19/14; C12P 19/02; C12M 41/32; C12M 45/09; C12M 21/18; C12M 41/48; C12M 41/36; D21C 5/005; D21C 1/00
See application file for complete search history.

(56) References Cited

U.S. PATENT DOCUMENTS

2004/0244925 A1* 12/2004 Tarasenko ................ D21C 1/04
                                                                 162/16
2010/0108567 A1*  5/2010 Medoff .................... C10G 3/00
                                                                 208/49
(Continued)

FOREIGN PATENT DOCUMENTS

WO    WO 2008/134885 A1    11/2008
WO    WO 2009/149766 A1    12/2009
WO    WO 2012/066042 A1     5/2012

OTHER PUBLICATIONS

Chundawat et al. "High-Throughput Microplate Technique for Enzymatic Hydrolysis of Lignocellulosic Biomass", *Biotechnology and Bioengineering* 99(6):1281-1294 (2008).
(Continued)

*Primary Examiner* — John Strege
(74) *Attorney, Agent, or Firm* — Myers Bigel, P.A.

(57) ABSTRACT

There is provided a method of producing a hydrolysate containing sugar from a lingocellulosic biomass, comprising the steps of: a) pretreating the lingocellulosic biomass in a pretreatment process to form a slurry comprising cellulosic particles; b) saccharification of the slurry obtained in step a) in the presence of hydrolytic enzymes in an enzymatic hydrolysis process to obtain a hydrolysate containing sugar; c) analyzing cellulosic particles present in the slurry obtained in step a) and/or cellulosic particles present in the enzymatic hydrolysis process during step b) using an image analysis method to obtain a data set; and d) controlling at
(Continued)

least one process parameter of the pretreatment process in step a) and/or enzymatic hydrolysis process in step b) in response to the data set obtained in step c). A corresponding system is also provided.

15 Claims, 6 Drawing Sheets

(51) Int. Cl.
    *C12M 1/34*     (2006.01)
    *C12M 1/40*     (2006.01)
    *C12M 1/36*     (2006.01)
    *C12M 1/00*     (2006.01)
    *C12P 19/02*     (2006.01)
    *C12P 19/14*     (2006.01)
    *C12P 7/10*     (2006.01)
    *D21C 1/00*     (2006.01)
    *D21C 5/00*     (2006.01)

(52) U.S. Cl.
    CPC ............. *C12M 41/48* (2013.01); *C12M 45/09* (2013.01); *C12P 7/10* (2013.01); *C12P 19/02* (2013.01); *C12P 19/14* (2013.01); *D21C 1/00* (2013.01); *D21C 5/005* (2013.01)

(56) References Cited

U.S. PATENT DOCUMENTS

2011/0293166 A1* 12/2011 Sinbar ................ G01N 21/3554
                                                      382/141
2012/0111714 A1* 5/2012 Court ........................ C10B 7/10
                                                      201/2.5
2014/0073820 A1* 3/2014 Bazzana ................ C12M 21/12
                                                      568/913
2016/0289704 A1* 10/2016 Medoff .................... C10G 3/00

OTHER PUBLICATIONS

Ehlers et al. "Particle size and packing characterization by diffuse light transmission", *Particuology* 10:619-627 (2012).
Huang et al. "Understanding the Key Factors for Enzymatic Conversion of Pretreated Lignocellulose by Partial Least Square Analysis", *Biotechnol. Prog.* 26:384-392 (2010).
Zitkova D. "Automation", http://www.pulpeye.com/wp-content/uploads/2012/02/Faxmil_s18-21_Auto1202_LOW.pdf(2012).
International Search Report for PCT/EP2014/051150 mailed Mar. 6, 2014.
International Preliminary Report on Patentability for PCT/EP2014/051150mailed Mar. 23, 2015.

* cited by examiner

IMAGE ANALYSIS BASED PROCESS CONTROL OF PROCESSES FOR PRODUCTION OF SUGAR FROM LIGNOCELLULOSIC BIOMASS

STATEMENT OF PRIORITY

This application is a 35 U.S.C. §371 national phase application of PCT Application No. PCT/EP2014/051150 filed Jan. 21, 2014, which claims priority to European Application No. 13152377.1 filed Jan. 23, 2013, the entire contents of each of which is incorporated by reference herein.

TECHNICAL FIELD

The present invention relates to methods for process control. In particular the invention relates to control of processes of pretreatment and hydrolysis of a lignocellulosic biomass in the production of sugars from the lignocellulosic biomass.

BACKGROUND

Biorefineries producing green chemicals from renewable resources offer an alternative to oil refineries based on dwindling supplies of petroleum and permit a move towards improved energy security. Lignocellulosic residues from forestry and agriculture are attractive as feedstocks, since they are abundant, relatively inexpensive, and are not used for food. Lignocellulose consists mainly of lignin and two classes of polysaccharides, cellulose and hemicellulose. The polysaccharides can be hydrolyzed to sugars which can be used as a platform chemical for the production of a host of other chemicals, for example by fermentation of the sugars in to various fermentation products, such as bioalcohols. The fermentation processes utilizes fermenting agents to convert the sugar in to fermentation products. One such fermenting agent is baker's yeast (*Saccharomyces cerevisiae*) which can be used to ferment sugars in to ethanol. The hydrolysis of cellulose is typically preceded by a pretreatment, in which the hemicellulose is degraded and the cellulose is made increasingly accessible to cellulolytic enzymes.

SUMMARY OF THE PRESENT DISCLOSURE

An efficient saccharification is dependent on that the pretreatment step has generated biomass of high enzymatic availability. If the pretreatment has not been severe enough, there is a risk that the enzymatic availability is too low. On the other hand, if the pretreatment is too severe, there is a risk that released sugars are degraded or that high levels of fermentation inhibitors and hydrolysis inhibitors are generated, which will reduce the efficiency of the following hydrolysis and fermentation steps. Thus, the present inventors have realized that it is highly desirable to be able to control the pretreatment process such that a pretreated biomass with a sufficiently high enzymatic availability is generated but where degradation of sugar and production of inhibitors remains low. However, regulation of the pretreatment process is challenging since the properties of the lignocellulosic feedstock going in to the process can vary with time throughout the process. This is in particularly true in a continuous process where different feedstock or feedstock with different characteristics is fed in to the process. For example the water content in the introduced feedstock might suddenly change which would affect the pre-treatment. In the art, one well established way of monitoring and controlling the pretreatment process involves manually taking out samples of pretreated biomass and analyzing the chemical properties of the samples in the laboratory to generate a value of the measured property. The value can be compared with a reference value and based on the comparison the pretreatment step can be adjusted by changing process parameters. Due to variations in the feedstock, changes in process parameters often need to be swift in order to save and/or correct an ongoing process. Therefore the inventors have come to the conclusion that the manual sampling methods and subsequent laboratory analyses described above often are too time consuming to be suitable in a method of controlling processes of production of sugars from lignocellulosic biomass. The inventors have thus realized that there is a need for a fast detection method which preferably can be used for continuous online or inline measurements. In the present disclosure the term "inline" measurements refers to measurements performed directly in a process line and the term "online" refers to measurements performed on a sample diverted from the main process line, e.g. in a bypass loop from the main process line. Both inline and online methods are distinguishable from offline methods where a sample is removed from the process and analyzed e.g. in a laboratory.

The present inventors have discovered that enzymatic availability of a pretreated lignocellulose biomass can be monitored online using an image analysis method and that the data received from the image analysis can be used to feedback control a pretreatment of a lignocellulosic biomass. The enzymatic availability of the biomass will influence the efficiency of the enzymatic hydrolysis. For example a low enzymatic availability might require higher enzyme concentrations. Thus the present inventors have also realized that the image analysis data also can be used to feed-forward control the enzymatic hydrolysis process.

Thus in a first aspect the present invention relates to a method of producing a hydrolysate containing sugar from a lingocellulosic biomass, comprising the steps of:
a) pretreating the lingocellulosic biomass in a pretreatment process to form a slurry comprising cellulosic particles;
b) saccharification of the slurry obtained in step a) in the presence of hydrolytic enzymes in an enzymatic hydrolysis process to obtain a hydrolysate containing sugar;
c) analyzing cellulosic particles present in the slurry obtained in step a) and/or cellulosic particles present in the enzymatic hydrolysis process during step b) using an image analysis method to obtain a data set; and
d) controlling at least one process parameter of the pretreatment process in step a) and/or enzymatic hydrolysis process in step b) in response to the data set obtained in step c).

A second aspect of the invention relates to a system for the preparation of a hydrolysate containing sugar from a cellulosic starting material, wherein the system is comprising:
i) a pretreatment arrangement for the preparation of a slurry comprising cellulosic particles from a cellulosic starting material, wherein the pretreatment arrangement is comprising an inlet and an outlet;
ii) an enzymatic hydrolysis reactor for saccharification of the slurry from the pretreatment comprising an inlet connected to the outlet of the pretreatment arrangement;
iii) an image capturing device comprising a light source capable of emitting light in the visible spectrum, a camera lens and a digital camera capable of capturing an image in the visible spectrum iv) an image processing device connected to the image capturing device and capable of processing data received from the image capturing device such that information about a size, shape and/or degree of darkness of the cellulosic particles can be obtained;

and wherein the image capturing device is arranged to capture images of cellulosic particles present:

in the slurry at a position in the connection between the outlet of the pretreatment arrangement and the inlet of the enzymatic hydrolysis arrangement;

in a slurry sample diverted from a position in the connection between the outlet of the pretreatment arrangement and the inlet of the enzymatic hydrolysis arrangement;

in the enzymatic hydrolysis reactor; and/or in a sample diverted from the enzymatic hydrolysis reactor.

DETAILED DESCRIPTION

Previously it has been reported that NIR spectroscopy based methods can be used for controlling processes of production of sugar from a lingocellulosic biomass, see WO2012/066042. This method is based on indirect measurements based on detection of molecular overtones and combination vibrations within or between molecules. The molecular overtone and combination bands seen in the near IR are typically very broad, leading to complex spectra; it can be difficult to assign specific features to specific chemical components. Multivariate (multiple variables) calibration techniques are often employed to extract the desired chemical information. Careful development of a set of calibration samples and application of multivariate calibration techniques is essential for near-infrared analytical methods.

The present invention relates to use of image analysis which is a direct analysis method involving extraction of meaningful information from images; in particular from digital images by means of digital image processing techniques. The prior art report of NIR-based methods are thus conceptually and technically clearly distinct from the subject matter of the present invention since it does not relate to image analysis based techniques.

The present inventors have developed a method of controlling a process of production of sugar from a lignocellulosic biomass. In contrast to methods previously described, relaying on chemical analysis of the biomass (or to NIR-based indirect methods as described above) the present method is based on image analysis of cellulosic particles in the pretreated biomass and correlation of at least one visual characteristic of the particles to the enzymatic availability of the pretreated biomass. The analyzed cellulosic particles comprise cellulose but, depending on the severity of the pretreatment, they might also comprise lignin and/or hemicellulose. The data generated from the analysis can be used for feedback control of the pretreatment process and/or for feed-forward control of the enzymatic hydrolysis process. A first aspect of the invention therefore relates to a method of producing a hydrolysate containing sugar from a lingocellulosic biomass, comprising the steps of:

a) pretreating the lingocellulosic biomass in a pretreatment process to form a slurry comprising cellulosic particles;

b) saccharification of the slurry obtained in step a) in the presence of hydrolytic enzymes in an enzymatic hydrolysis process to obtain a hydrolysate containing sugar;

c) analyzing cellulosic particles present in the slurry obtained in step a) and/or cellulosic particles present in the enzymatic hydrolysis process during step b) using an image analysis method to obtain a data set; and d) controlling at least one process parameter of the pretreatment process in step a) and/or enzymatic hydrolysis process in step b) in response to the data set obtained in step c).

One advantage with the present invention is that the analysis can be performed online. Thereby, time consuming manual sampling methods and subsequent laboratory analyses used for controlling process parameters in the prior art can be avoided. This is critically important since changes in process parameters often need to be swift in order to save and/or correct an ongoing process. This is especially true in continuous and semi-continuous processes where feedstock going in to the process can vary with time throughout the process. If the method is an online method, a sample comprising cellulosic particles can be diverted, from a position after the pretreatment in a pretreatment reactor but prior to an enzymatic hydrolysis step. The sample can then be directed to an image capturing device where images of cellulosic particles are captured. Images can thereafter be processed by an image processing device using software adapted to execute image analysis to generate the data set, which can be used for controlling the process. It might also be possible to capture images directly inline at a position after the pretreatment in the pretreatment reactor but prior to the enzymatic hydrolysis step. Since the acquired data set also can be used for control of the enzymatic hydrolysis, a sample comprising cellulosic particles can also be diverted from the enzymatic hydrolysis reactor, to the image capturing device during the enzymatic hydrolysis process. Thus, in one embodiment step c) is an online or inline analysis. In a preferred embodiment step c) is an online analysis. In one embodiment step c) is an online analysis and the method further includes a step of diverting a sample comprising cellulosic particles after the pretreatment process in step a) but prior to the enzymatic hydrolysis process in step b) and the analyzing of cellulosic particles in step c) is performed on the said diverted sample. In one embodiment, step c) is an online analysis and the method includes a step of diverting a sample comprising cellulosic particles from the enzymatic hydrolysis process in step b) and the analyzing of cellulosic particles in step c) is performed on the said diverted sample. In one embodiment the image analysis in step c) is an Ultraviolet-visible spectrum image analysis. In a preferred embodiment the image analysis in step c) is a visible spectrum image analysis. In one embodiment step c) includes taking a digital image in the Ultraviolet-visible spectrum or and processing the image using an algorithm such that the data set is obtained. In a preferred embodiment step c) includes taking a digital image in the visible range and processing the image using an algorithm such that the data set is obtained. In one embodiment step c) comprises processing data using a software adapted to execute image analysis.

The present inventors have demonstrated that online image analysis methods according to the present invention can be used to monitor enzymatic availability of a pretreated lignocellulosic biomass. Enzymatic availability is a measure of how susceptible the substrate is to the hydrolytic enzymes and the purpose with the pretreatment is to increase enzymatic availability. A reason of low enzymatic availability of a pretreated biomass is that the pretreatment has not been severe enough. Therefore, if a low enzymatic availability is detected, the pretreatment process can be controlled by increasing the severity of the pretreatment. This can be achieved by increasing one or more severity parameters, such as increasing the temperature, pressure and/or residence time in the pretreatment reaction. If the pretreatment is an acidic process the severity can also be increased by decreasing a pH value of the pretreatment process and if the pretreatment is an alkaline process the severity can be increased by increasing a pH value of the pretreatment process. When the pretreatment is acidic, the pH value may be decreased by increasing the amount acid catalyst (e.g. $H_2SO_4$ or $SO_2$) added. When the pretreatment is alkaline, the pH value may be increased by increasing the amount of alkali catalyst (e.g. NaOH) added. Furthermore, detection of low enzymatic availability of the pretreated biomass can also be used for feed-forward regulation of the enzymatic hydrolysis process. Since a pretreated biomass with a low enzymatic availability is harder to hydrolyze, parameters of the hydrolysis can be adapted to facilitate proper hydrolysis of the pretreated biomass. For example, more enzymes might be added to the enzymatic hydrolysis reaction or a residence time of the cellulosic material in the enzymatic hydrolysis process might be increased. Since different kinds of biomasses demands different severity of the pretreatment the process can also be controlled by altering the composition of the biomass used in the pretreatment step. For example, lingocellulosic biomass from hard wood and soft wood generally requires harsher pretreatment than for example agricultural residues. Thus if a too low enzymatic availability is detected the process can be controlled by using a biomass composition comprising a lower proportion of biomass requiring a high severity of the pretreatment (e.g. wood) and a higher proportion of biomass requiring a lower severity (e.g. agricultural residues). Generally the biomass is chopped into smaller pieces prior to the pretreatment step. For example lumber and other wood residues are generally chipped into wood chips. A biomass with large particle size (e.g. large wood chips) generally requires harsher pretreatment than biomass with smaller particle size (e.g. smaller wood chips). Therefore, if a too low enzymatic availability is detected the process can be controlled by increasing a degree of disintegration of the biomass prior to the pretreatment in step a. Vice versa, if the enzymatic availability is high the process can be controlled by using a biomass composition comprising a higher proportion of biomass requiring a high severity of the pretreatment (e.g. wood) and/or by decreasing a degree of disintegration of the biomass prior to the pretreatment in step a). Thus, in one embodiment the process parameter controlled in step d) is selected from:

a pH-value of the pretreatment process;
a residence time of the cellulosic material in the pretreatment process;
a temperature of the pretreatment process;
a pressure of the pretreatment process;
an amount of hydrolytic enzymes added in the enzymatic hydrolysis process;
a residence time of the cellulosic material in the enzymatic hydrolysis process;
a biomass composition of the lingocellulosic biomass pretreated in step a); and
a degree of disintegration of the biomass prior to the pretreatment in step a)

In one embodiment the data set obtained in c) is used for determining the enzyme accessibility of the cellulosic particles. The image analysis can be used to detect any feature of the cellulosic particles that correlates to the enzymatic availability of the cellulosic particles. For example the present inventors have demonstrated that determination of the size of the cellulosic particles can be used to determine or estimate the enzymatic availability. Specifically, the inventors have demonstrated that cellulosic particles of smaller size has higher enzymatic availability than larger particles. The size of the cellulosic particles can for example be measured as the projected area of the particles. The inventors have further demonstrated that the shape of the particles can be used to determine or estimate the enzymatic availability. By assigning a "form factor" to the cellulosic particles, the inventors have shown that some forms are correlated to higher enzymatic availability. In this case the form factor was a measure of how spherical or elongated the particles are. A form factor of 1 corresponded to a completely circular object whereas a form factor close to zero is a very elongated object. It can clearly be seen that there exists an optimal form factor in between these two extremes. This demonstrates that image analysis can be used for detection of the shape of cellulosic particles and that the detected shape can be used for estimation or determining the enzymatic availability and thus for process control of process for production of sugars from lingocellulosic biomass. Similarly, the present inventors have also demonstrated that the darkness of the particles detected in the image analysis also correlates to enzymatic availability. Darker particles correlates with higher enzymatic availability and brighter particles correlates with lower enzymatic availability. Therefore, in one embodiment step c) further includes determining a size, a shape, and/or a degree of darkness of the cellulosic particles based on the obtained data set. In one embodiment, the size is measured as the projected area. In one embodiment, a numerical value of the size, shape and/or degree of darkness of the cellulosic particles is obtained based on the obtained data set. In one embodiment the numerical value is a mean or median value of analyzed cellulosic particles captured on one or more images. In order to get a high statistical significance of the numerical value it is preferable that a high number of particles are analysed from the captured picture. It is therefore preferable that the majority, preferably all of the particles that can be identified as particles from the captured image are analyzed. The size of the particles that can be detected depends on the resolution of the camera used in the image capturing device. For example if the camera has a resolution of 73 pixels per mm the particles need to have a projected are of at least 0.014 mm in order to be detected. It also possible to introduce a threshold such that the smallest particles are not detected as particles. For example the threshold can be set such that particles covering less than 50 pixels or less than 10 pixels are not detected. In order to get a high statistical significance of the numerical value it is also beneficial that the captured picture covers a relatively large number of particles. Therefore it is preferred that the captured picture covers an area of at least 10 mm², more preferably at least 50 mm², more preferably at least 100 mm². However if the area is to big the resolution will not be good enough. Therefore in a preferred embodiment the captured picture covers an area of between 100-3000 mm², more preferably between 100-1000 mm², most preferably between 200-600 mm². To get a high statistic significance it is beneficial that a high number of pictures is taken from the sample to be analysed in step c). Therefore in one embodiment step c) includes taking at least 20, preferably at least 50, preferably at least 100, preferably at least 200 such as at least 500 pictures of samples comprising the slurry obtained in step a) and/or samples comprising cellulosic particles present in the enzymatic hydrolysis process during step b).

In one embodiment the obtained numerical value is compared to a reference value and if the obtained numerical value differs from the reference value, at least one process parameter of the pretreatment process and/or enzymatic hydrolysis process is adjusted in response to the difference to control the pretreatment process and/or the enzymatic hydrolysis process. In one embodiment the reference value is an interval. In one embodiment the size and/or a degree of darkness of cellulosic particles is determined in step c) and compared to a reference value and if the size is larger than the reference value and/or if the degree of darkness of the cellulose particles are lower than the reference value at least one of the following process adjustments are performed:
   increase of the severity of the pretreatment process;
   increase of the efficiency of the enzymatic hydrolysis process; and
   increase a degree of disintegration of the biomass prior to the pretreatment in step a).

In this respect the meaning of the term "increase of the efficiency of the enzymatic hydrolysis process" means that parameters are adjusted such that enzymatic hydrolysis works more efficiently such that more sugar is produced from the lignocellulosic biomass in the hydrolysis step. The efficiency of the enzymatic hydrolysis process can for example be increased by increasing the amount of hydrolytic enzymes added to the enzymatic hydrolysis process or by increasing the residence time of the lignocellulosic biomass in the enzymatic hydrolysis.

If the pretreatment is too harsh sugars can be degraded in the pretreatment and higher amounts of fermentation inhibitors and hydrolysis inhibitors might be formed. If to harsh pretreatment is detected using the image analysis method according to the present invention the pretreatment process can be feedback controlled by decreasing the severity of the pretreatment. Furthermore, if the pretreated lignocellulosic biomass has a very high enzymatic availability it might be possible to use less enzyme in the enzymatic hydrolysis process. This is desirable since the enzymes are quite expensive and stands for a large proportion of the costs in the production of sugars from lignocellulosic biomass. Thus, in one embodiment the size and/or degree of darkness of cellulosic particles is determined in step c) and compared to a reference value and if the size is smaller than the reference value and/or if the degree of darkness of the cellulose particles are higher than the reference value at least one of the following process adjustments are performed:
   decrease of the severity of the pretreatment process;
   decrease of the efficiency of the enzymatic hydrolysis process; and
   decrease a degree of disintegration of the biomass prior to the pretreatment in step a).

In one embodiment the severity of the pretreatment process is increased by increasing a pressure, temperature and/or residence time in the pretreatment and/or by changing a pH in the pretreatment process. In one embodiment the severity of the pretreatment is decreased by decreasing a pressure, temperature and/or residence time in the pretreatment and/or by changing a pH in the pretreatment process. In one embodiment the pretreatment process in an acidic pretreatment process and the severity of the pretreatment process is increased by decreasing a pH in the pretreatment process. In one embodiment the pretreatment process in an acidic pretreatment process and the severity of the pretreatment process is decreased by increasing a pH in the pretreatment process. In one embodiment the pretreatment process in an alkaline pretreatment process and the severity of the pretreatment process is increased by increasing a pH in the pretreatment process. In one embodiment the pretreatment process in an alkaline pretreatment process and the severity of the pretreatment process is decreased by decreasing a pH in the pretreatment process. In one embodiment the efficiency of the enzymatic hydrolysis is increased by increasing the amount of hydrolytic enzyme in the enzymatic hydrolysis process and/or by increasing a residence time of the cellulosic material in the enzymatic hydrolysis process. In one embodiment the efficiency of the enzymatic hydrolysis is decreased by decreasing the amount of hydrolytic enzyme in the enzymatic hydrolysis process and/or by decreasing a residence time of the cellulosic material in the enzymatic hydrolysis process. In one embodiment the size of cellulosic particles is determined in step c) and compared to a reference value and if the size is larger than the reference value at least one of the following process adjustments are performed:
   decreasing a pH-value of the pretreatment process if the pretreatment is an; acidic pretreatment process;
   increasing a pH-value of the pretreatment process if the pretreatment is an alkaline pretreatment process;
   increasing a residence time of the cellulosic material in the pretreatment process;
   increasing a temperature of the pretreatment process;
   increasing a pressure of the pretreatment process;

increasing an amount of hydrolytic enzymes added in the enzymatic hydrolysis process;

increasing a residence time of the cellulosic material in the enzymatic hydrolysis process; and increasing a degree of disintegration of the biomass prior to the pretreatment in step a).

In one embodiment the size of cellulosic particles is determined in step c) and compared to a reference value and if the size is smaller than the reference value at least one of the following process adjustments are performed:

increasing a pH-value of the pretreatment process if the pretreatment is an acidic pretreatment process;

decreasing a pH-value of the pretreatment process if the pretreatment is an alkaline pretreatment process;

decreasing a residence time of the cellulosic material in the pretreatment process;

decreasing a temperature of the pretreatment process;

decreasing a pressure of the pretreatment process;

decreasing an amount of hydrolytic enzymes added in the enzymatic hydrolysis process;

decreasing a residence time of the cellulosic material in the enzymatic hydrolysis process; and decreasing a degree of disintegration of the biomass prior to the pretreatment in step a).

In one embodiment a degree of darkness of cellulosic particles is determined in step c) and compared to a reference value and if the degree of darkness of the cellulose particles are lower than the reference value at least one of the following process adjustments are performed:

decreasing a pH-value of the pretreatment process if the pretreatment is an acidic pretreatment process;

increasing a pH-value of the pretreatment process if the pretreatment is an alkaline pretreatment process;

increasing a residence time of the cellulosic material in the pretreatment process;

increasing a temperature of the pretreatment process;

increasing a pressure of the pretreatment process;

increasing an amount of hydrolytic enzymes added in the enzymatic hydrolysis process;

increasing a residence time of the cellulosic material in the enzymatic hydrolysis process; and increasing a degree of disintegration of the biomass prior to the pretreatment in step a).

In one embodiment a degree of darkness of cellulosic particles is determined in step c) and compared to a reference value and if the degree of darkness of the cellulose particles are higher than the reference value at least one of the following process adjustments are performed:

increasing a pH-value of the pretreatment process if the pretreatment is an acidic pretreatment process;

decreasing a pH-value of the pretreatment process if the pretreatment is an alkaline pretreatment process;

decreasing a residence time of the cellulosic material in the pretreatment process;

decreasing a temperature of the pretreatment process;

decreasing a pressure of the pretreatment process;

decreasing an amount of hydrolytic enzymes added in the enzymatic hydrolysis process;

decreasing a residence time of the cellulosic material in the enzymatic hydrolysis process; and decreasing a degree of disintegration of the biomass prior to the pretreatment in step a).

In one embodiment at least two, preferably all of the following characteristics of the cellulosic particles are analyzed in step c):

size, shape and degree of darkness, and wherein the data is processed with a multivariate data analysis method to obtain the data set.

The pretreatment may involve one or several pretreatment methods known to the skilled person. As an example, the pretreatment may be performed at elevated temperature with acid, typically dilute mineral acid, such as sulfuric acid. The pre-treatment may involve impregnation, which refers to impregnation of the cellulosic material with an impregnation fluid, followed by heating. In the case of acid pretreatment, the impregnation fluid may be an acid solution, such as a mineral acid solution. The impregnation may also be performed with a gas, such as a $SO_2$ gas or $CO_2$ gas, or with the combination of a gas with a liquid to obtain e.g. sulfurous acid or carbonic acid. The elevated temperature may be achieved by steaming, a process used to drive air out from the cellulosic biomass to facilitate hydrolysis of the cellulose. Steaming is a well-known method for pretreating e.g. lignocellulosic biomass. As another example, the pretreatment may involve steam explosion, a process that combines steam, hydrolysis and rapid pressure releases for rupturing cellulosic fibers. Other pretreatment methods known to the skilled person which can be used in the present invention includes alkaline pre-treatment and organosolv pre-treatment methods.

However, in one preferred embodiment the pretreatment process in step a) is an acidic pretreatment process. In one embodiment the pretreatment is a dilute acid pretreatment. In one embodiment the acidic pretreatment is a pretreatment using sulfuric acid, $SO_2$ and/or sulfurous acid. In one embodiment the pretreatment involves steam explosion. In one embodiment the pretreatment is preformed at a temperature of 120-250° C. and/or a pH of less than 2.

As discussed above sugar produced from lignocellulosic biomass can be used as a platform chemical for production of a number of different green chemicals. A particularly suitable method of producing green chemicals from sugar involves fermentation of the sugars in to fermentation products using a fermenting organism. Thus, in one embodiment the method further comprises a step e) producing a target chemical from the hydrolysate containing sugar obtained in b) In one embodiment step e) is a fermentation step and the target chemical is a fermentation product. In one embodiment the fermentation in step e) is performed by a fermenting organism. In one embodiment the fermenting organism is bacteria and/or yeast. In one embodiment the fermenting organism is yeasts from the genera *Saccharomyces*, *Pichia* or *Candida*. In one embodiment the fermenting organism is bacteria from the genera *Zymomonas* or *Escherichia*. In one embodiment the fermentation product is selected from alcohols, acids, alkanes, alkenes, aromatics, aldehydes, ketones, biopolymers, proteins, peptides, amino acids or vitamins. In one embodiment the fermentation product is ethanol. In one embodiment the enzymatic hydrolysis process in step b) and the fermentation in step e) are performed separately in a separate hydrolysis and fermentation process. In one embodiment the enzymatic hydrolysis process in step b) and the fermentation in step e) is performed simultaneously in a simultaneous saccharification and fermentation process.

In one embodiment the lignocellulosic biomass is agricultural residues or wood material. In one embodiment the lignocellulosic biomass is hard wood and/or soft wood. In one embodiment the lignocellulosic biomass is spruce, pine, birch, oak, *eucalyptus*, switch grass, *eucalyptus salix*, banagrass, arundo, corn cobs, corn stover, oat hulls, sugar cane, bagasse, straw from barley, straw from wheat, straw from oat, straw from triticale and/or straw from rye. In a preferred embodiment the lignocellulosic biomass is wood chips.

Several different hydrolytic enzymes can be used in the methods according to the invention. In one embodiment the hydrolytic enzymes is a cellulase, endoglucanase, exoglucanase, cellobiohydrolase, β-glucosidase, xylanase, endoxylanase, exoxylanase, β-xylosidase, arabinoxylanase, mannanase, galactanase, pectinase, glucuronase, amylase, α-amylase, β-amylase, glucoamylase, α-glucosidase, isoamylase, and/or any enzymes in the group of enzymes found in EC 3.2.1.x, such as EC 3.2.1.4, where EC is the Enzyme Commission number. In a preferred embodiment at least one endoglucanase, at least one exoglucanase and at least one β-glucosidase is present in step b). In one embodiment an amount of endoglucanase, exoglucanase and/or β-glucosidase is added to the enymatic hydrolys process in step d) and the amount of added endoglucanase, exoglucanase and/or β-glucosidase is selected based on the data set obtained in step c).

A second aspect of the present invention relates to a system for the preparation of a hydrolysate containing sugar from a cellulosic starting material, wherein the system is comprising:
i) a pretreatment arrangement for the preparation of a slurry comprising cellulosic particles from a cellulosic starting material, wherein the pretreatment arrangement is comprising an inlet and an outlet;
ii) an enzymatic hydrolysis reactor for saccharification of the slurry from the pretreatment comprising an inlet connected to the outlet of the pretreatment arrangement;
iii) an image capturing device comprising a light source capable of emitting light in the visible spectrum, a camera lens and a digital camera capable of capturing an image of in the visible spectrum
iv) an image processing device connected to the image capturing device and capable of processing data received from the image capturing device such that information about a size, shape and/or degree of darkness of the cellulosic particles can be obtained;
and wherein the image capturing device is arranged to capture images of cellulosic particles present:
  in the slurry at a position in the connection between the outlet of the pretreatment arrangement and the inlet of the enzymatic hydrolysis arrangement;
  in a slurry sample diverted from a position in the connection between the outlet of the pretreatment arrangement and the inlet of the enzymatic hydrolysis arrangement;
  in the enzymatic hydrolysis reactor; and/or
  in a sample diverted from the enzymatic hydrolysis reactor.

For practical reasons it is hard to arrange a camera inline in between the outlet of the pretreatment arrangement and the inlet of the enzymatic hydrolysis arrangement. Moreover, in continuous process the slurry of pretreated material is moving from the pretreatment arrangement to the enzymatic hydrolysis reactor and thus it will be hard to capture a picture inline. Therefore it is preferred that the sample to be detected is diverted and analyzed online. Therefore, in one embodiment the system is further comprising a slurry sample outlet provided on the connection between the outlet of the pretreatment arrangement and the inlet of the enzymatic hydrolysis reactor, wherein the image capturing device is arranged to capture images of cellulose particles within a slurry sample diverted through the slurry sample outlet.

It is also challenging to analyze cellulosic particles within the enzymatic hydrolysis reactor inline since the cellulosic particles in the reactor is moving during the process. Thus in a preferred embodiment the system is further comprising a hydrolysate sample outlet provided on the enzymatic hydrolysis reactor, and the image capturing device is arranged to capture images of cellulose particles within a hydrolysate sample diverted through the hydrolysate sample outlet.

In one embodiment the system comprises at least one sample zone and the sample comprising cellulosic particles is directed to the sample zone and the image capturing device is arranged to capture an image of cellulosic particles present in the sample zone. In one embodiment the sample zone is connected to the hydrolysate sample outlet. In one embodiment the sample zone is connected to the slurry sample outlet. In one embodiment the sample zone comprises a flow cell. In one embodiment the system comprises a sample preparation unit. In one embodiment the sample preparation unit comprises a tank for dilution of a sample. In one embodiment the sample preparation unit comprises means for adjusting the temperature of the sample. In one embodiment the sample preparation unit comprises means for adjusting the pH of the sample. In one embodiment the sample preparation unit is arranged in between the hydrolysate sample outlet and the sample zone. In one embodiment the sample preparation unit is arranged in between the slurry sample outlet and the sample zone. In one embodiment the system comprises a pump for pumping a sample from the sample preparation unit into the sample zone. In one embodiment the visible light digital camera is a CCD camera or a CMOS camera, in one embodiment the camera has a resolution of at least 20 pixels/mm, such as at least 50 pixels/mm, such as at least 73 pixels/mm. In one embodiment the light source is a light-emitting diode. In one embodiment the image processing device comprises a computer. In one embodiment the image processing device comprises software adapted to execute image analysis.

The various embodiments discussed in connection with the first aspect apply to the second aspect mutatis mutandis. Likewise, the various embodiments discussed in connection with the second aspect apply to the first aspect mutatis mutandis.

EXAMPLES

Pretreated slurry samples were prepared by pretreatment of spruce wood chips using $SO_2$-catalyzed steam explosion using different severity parameters of the pretreatment. The pretreated samples were subjected to enzymatic hydrolysis to determine the enzymatic availability of the different samples. The enzymatic hydrolysis was performed at 5% (SS), at 35° C. using the enzyme mixture cellic C-tec (Novozymes). The enzymatic availability was measured in grams of glucose per liter liquid after 48 hours hydrolysis time; the glucose concentration was measured using a commercial D-Glukos enzyme kit. Ten samples were prepared for the trial with 3.0 g dry matter in each sample which corresponded to around 20 ml of slurry. The enzymatic availability of the different samples is shown in table 1.

TABLE 1

| Name | Date | Glucose after screening (g/L) |
|---|---|---|
| Ref1:1 | Ref-slurry | 14.7 |
| Ref2:1 | Ref-slurry | 14.7 |
| 7/5 1:1 | 2011 May 7 07:00 | 11 |
| 7/5 2:1 | 2011 May 7 00:00 | 11 |

TABLE 1-continued

| Name | Date | Glucose after screening (g/L) |
|---|---|---|
| 19/8 1:1 | 2011 Aug. 19 07:00 | 17.5 |
| 19/8 2:1 | 2011 Aug. 19 07:00 | 17.5 |
| 5/10 1:1 | 2011 May 10 07:00 | 14.52 |
| 5/10 2:1 | 2011 May 10 07:00 | 14.52 |
| 9/10 1:1 | 2011 Sep. 10 08:00 | 12.95 |
| 9/10 2:1 | 2011 Sep. 10 08:00 | 12.95 |

Figure 1:
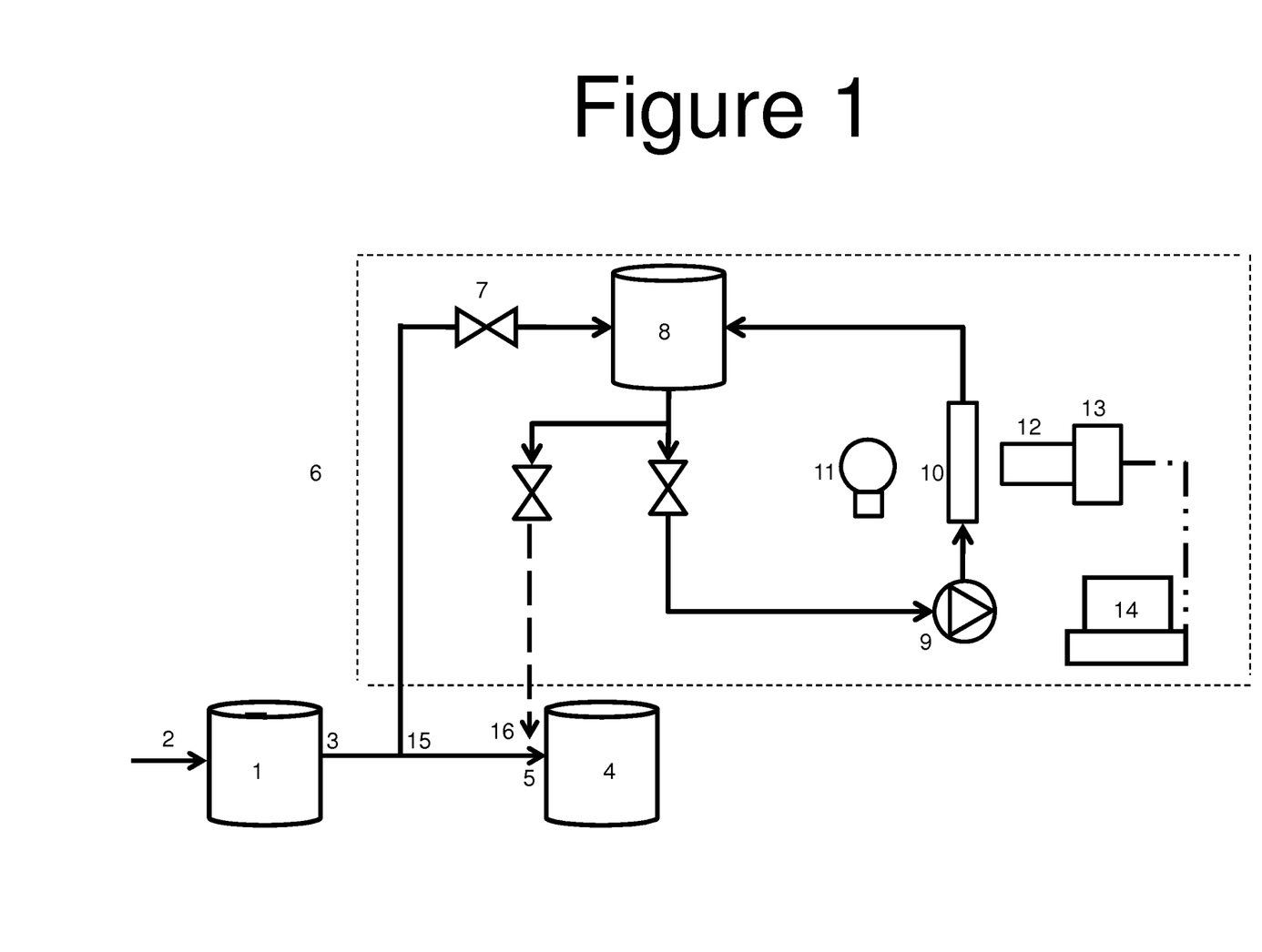
FIG. 1 shows a system for the preparation of a hydrolysate containing sugar from a cellulosic starting material according to the present invention

The instrumental system for the analysis was based on the DotEye analyzer system (PulpEye AB, Örnsköldsvik, Sweden), and corresponds to the analyzing unit (6) shown in FIG. 1. The samples were introduced through a sample inlet valve (7) and was thereafter diluted to proper consistency, in the sample dilution tank (8). After sample preparation, 2000 images were captured, saved and analyzed for each sample. Each sample was run 2 times giving a total of 4000 images per sample. The system was cleaned with water after each sample run. The total cycle time was about 5 minutes. The images were analyzed and processed using algorithms to pick out the characteristics of the particles in the solution. The results contain various parameters describing the particles physical properties, including size, shape and grey level. The degree of darkness is inversely related to the grey level, i.e. a low value of the grey level corresponds to a high degree of darkness (i.e. darker particles) and a high value of the grey level correspond to a low degree of darkness (i.e. brighter particles). The value 0 in the grey level scale shown in the figures corresponds to a black particle. The results presented in examples 1-3 clearly demonstrate that the shape, form and/or degree of darkness of particles in a pretreated slurry can be used to evaluate the enzymatic availability of a pretreated biomass.

Example 1

Figure 2A:
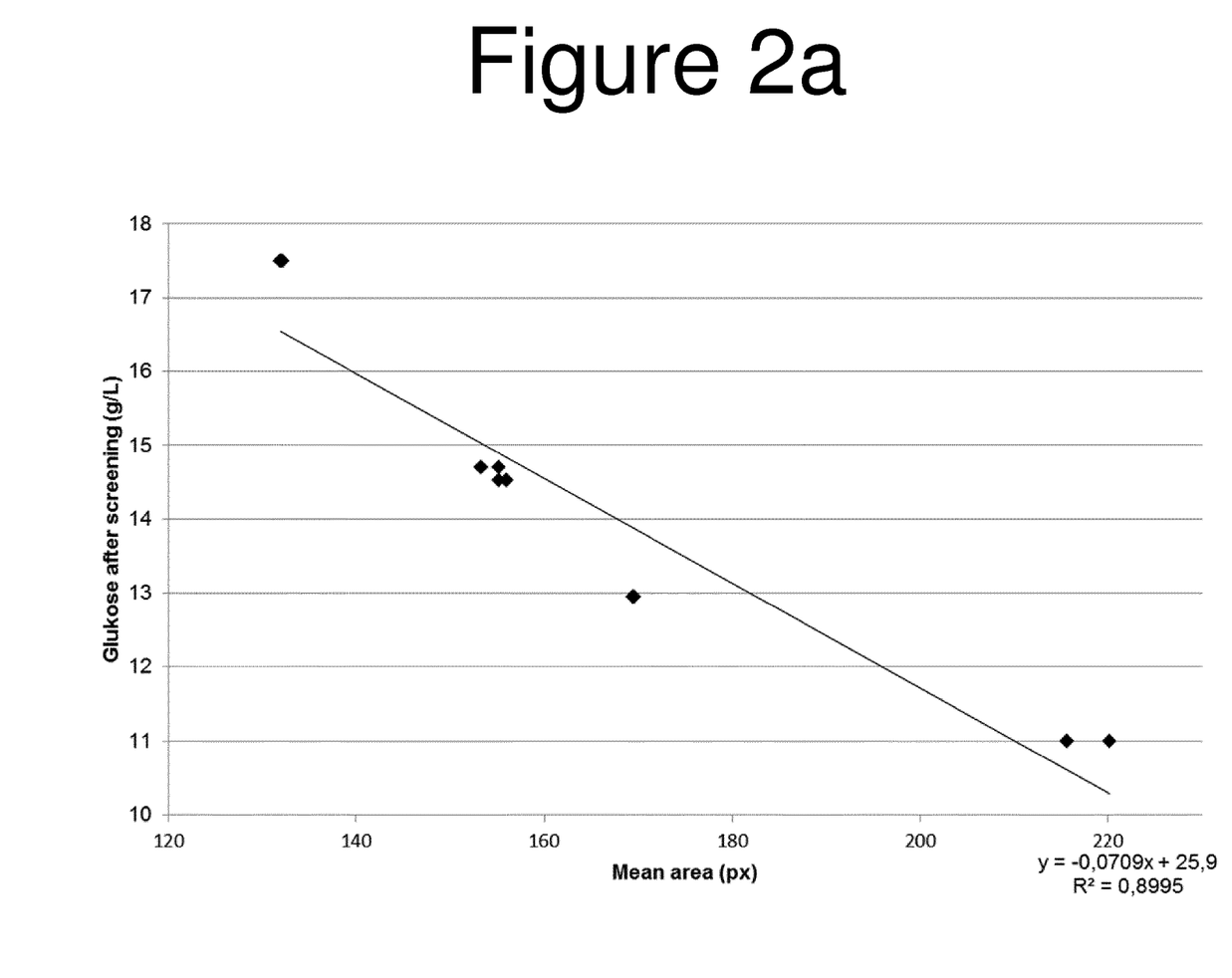
FIG. 2a shows the relation between particle size and enzymatic availability (measured as glucose production) of pretreated lignocellulosic slurries. The X-axis shows mean projected area of the particles (pixels) and the Y-axis shows glucose concentration (g/l).
Figure 2B:
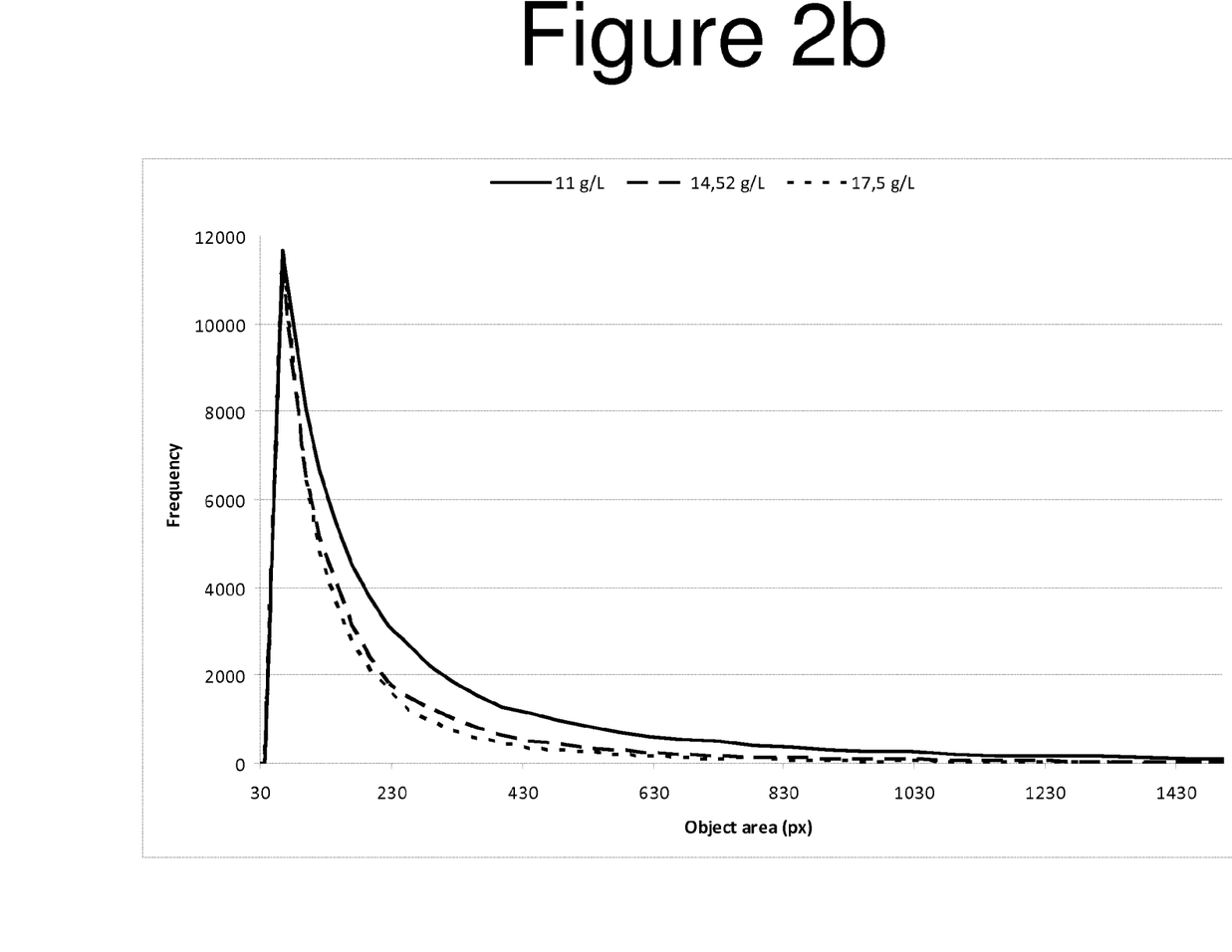
FIG. 2b shows the size distribution of the detected objects from slurries with different enzymatic availabilities (measured as glucose production). The X-axis shows projected area of the particles (pixels) and the Y-axis shows frequency (i.e. number of particles).

As shown in FIG. 2a the mean area of the particles in the samples correlates well with enzymatic availability. Smaller particles give higher glucose yields in the screening. The size distribution plot (FIG. 2b) also demonstrates that higher amount of large particles in the samples correlates with low enzymatic availability whereas higher amounts of small particles correlate with high enzymatic availability.

Example 2

Figure 3A:
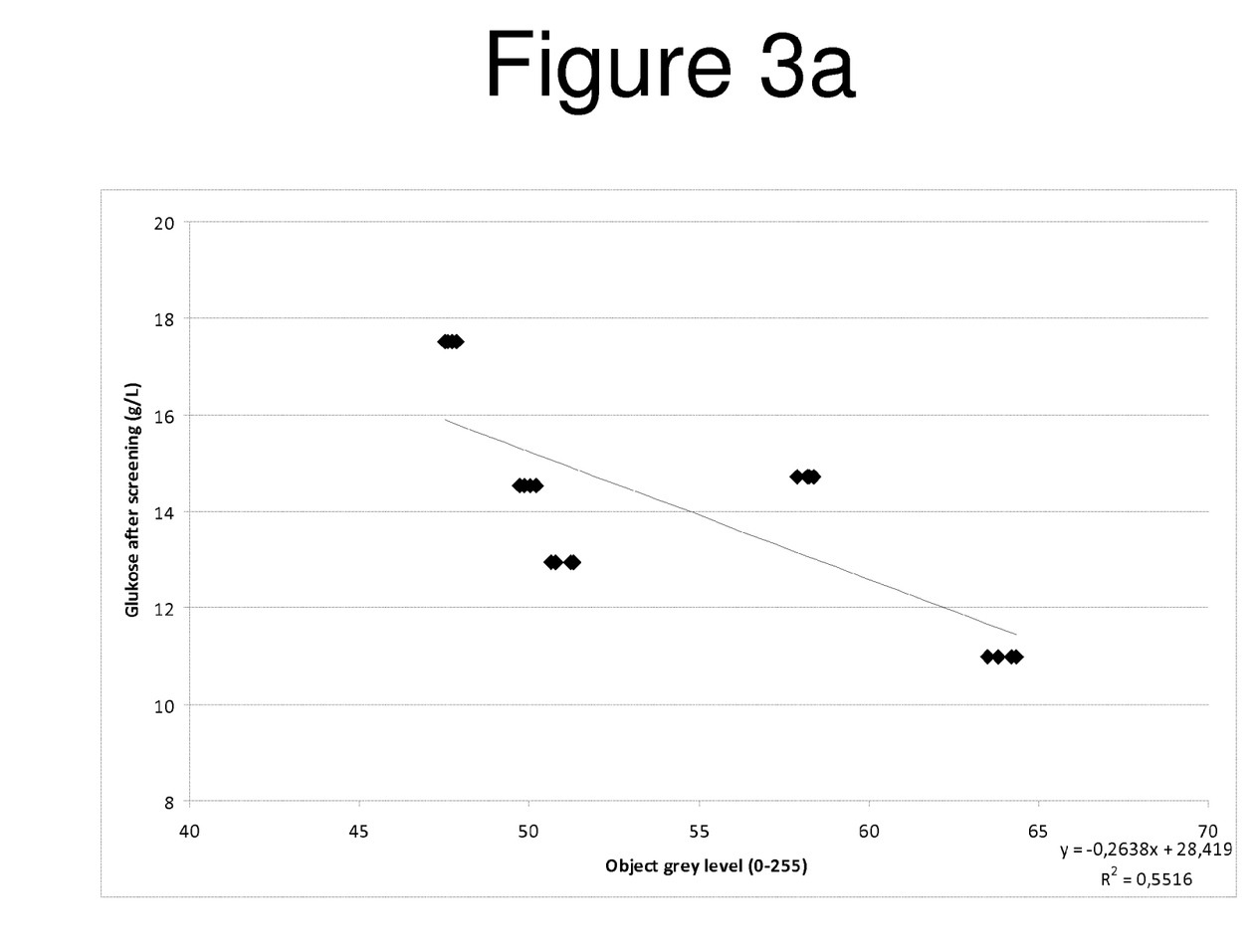
FIG. 3a shows the relation between degree of darkness of the particles and enzymatic availability (measured as glucose production) of pretreated lignocellulosic slurries. The X-axis shows the grey level and the Y-axis shows glucose concentration (g/l). The degree of darkness is inversely related to the grey level, i.e. a low value of the grey level corresponds to a high degree of darkness and a high value of the grey level correspond to a low degree of darkness. The value 0 in the grey level scale shown in the figure corresponds to a black particle.
Figure 3B:
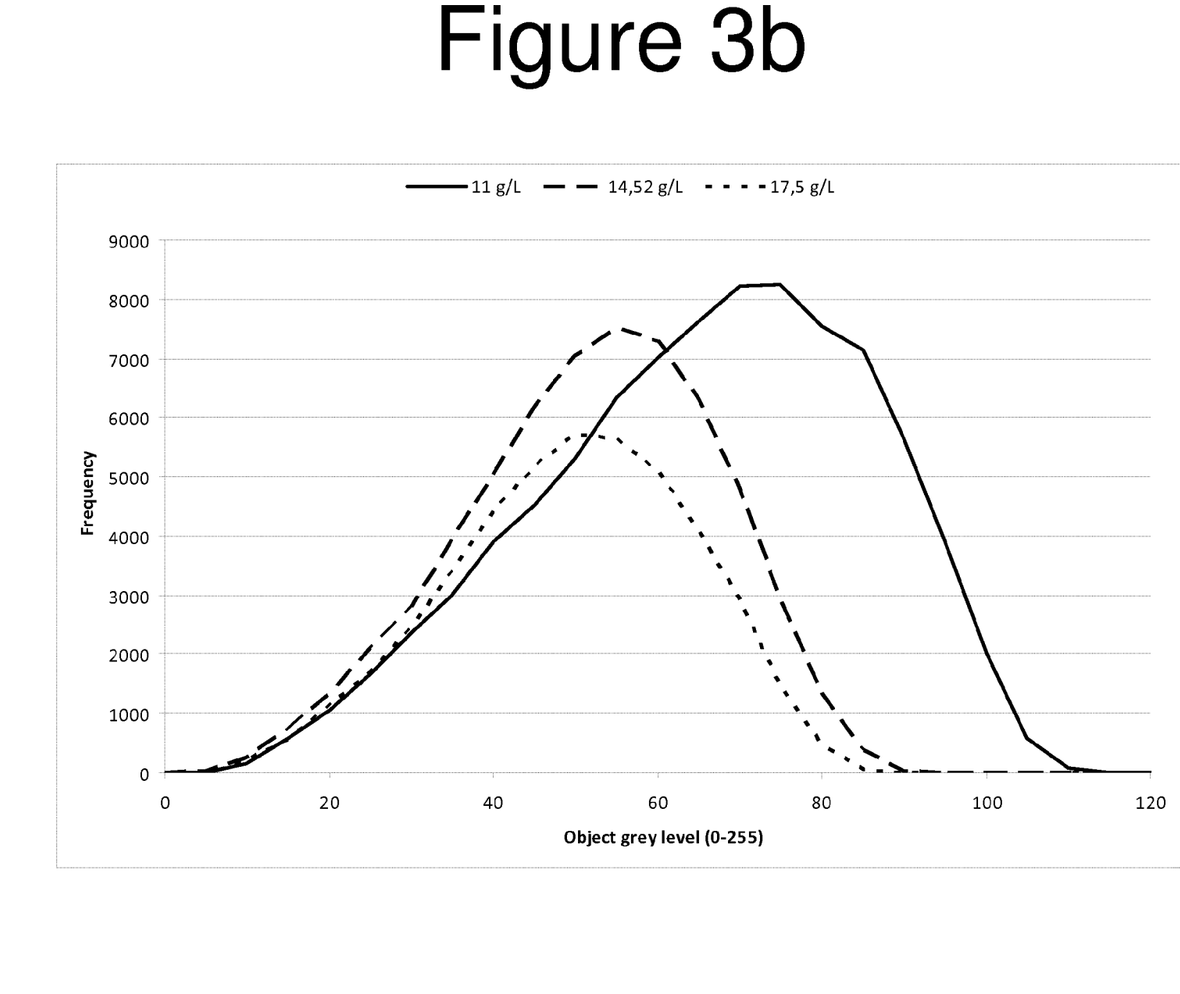
FIG. 3b shows the degree of darkness distribution of the detected objects from slurries with different enzymatic availabilities (measured as glucose production). The X-axis shows degree the grey level of the particles and the Y-axis shows frequency (i.e. number of particles). The degree of darkness is inversely related to the grey level, i.e. a low value of the grey level corresponds to a high degree of darkness and a high value of the grey level correspond to a low degree of darkness. The value 0 in the grey level scale shown in the figure corresponds to a black particle.

The grey level or darkness of the particles in the slurry also correlates with enzymatic availability. FIG. 3a shows mean grey level ranging from 0-255 where 0 is black and 255 is white. As shown in FIG. 3a, darker objects results in higher yields than bright objects. This correlation is also evident from FIG. 3b, which shows a distribution plot for three different samples with different enzymatic availability Example 3

Figure 4:
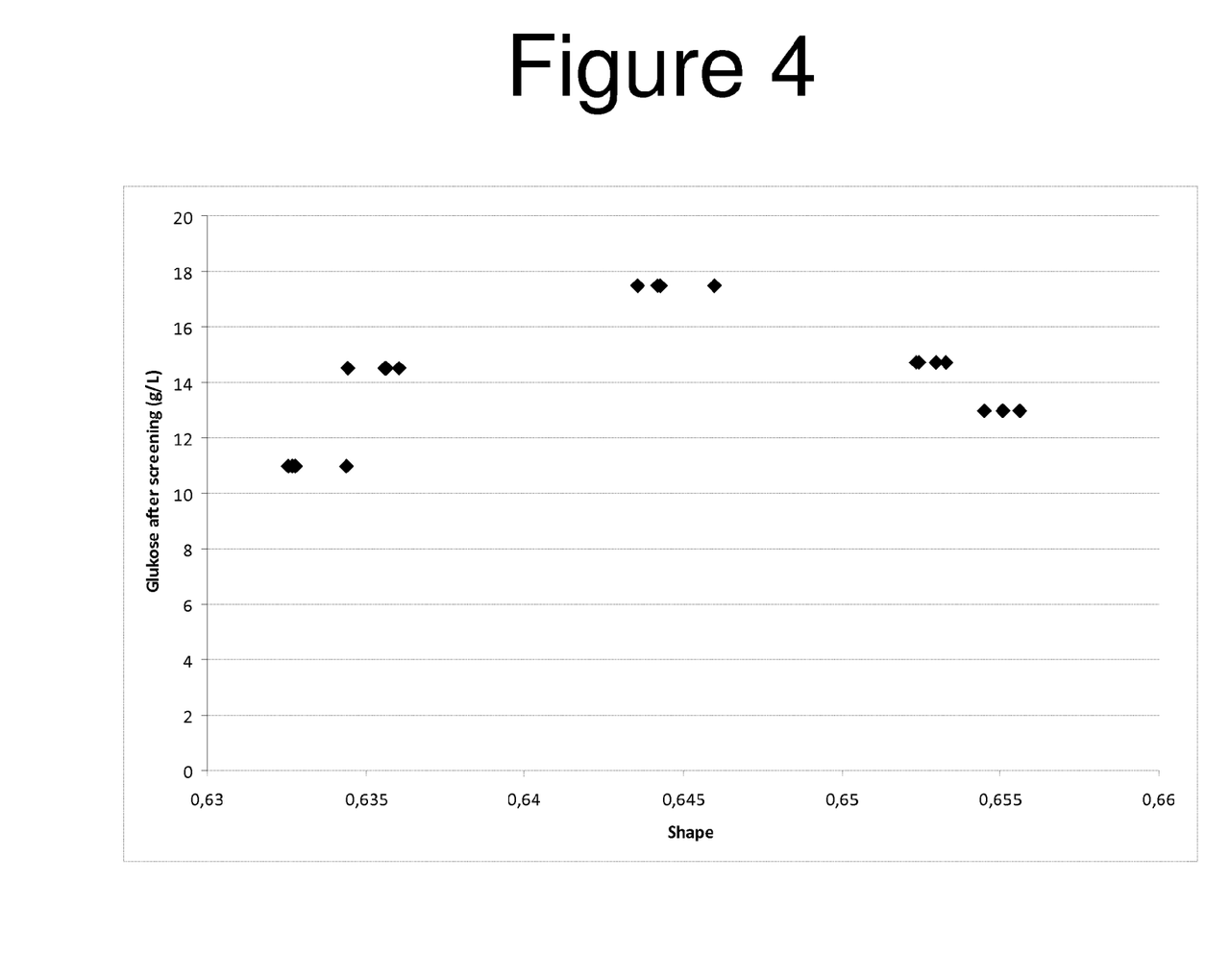
FIG. 4 shows the relation between particle form and enzymatic availability (measured as glucose production) of pretreated lignocellulosic slurries. The X-axis shows the form factor (describing how round or elongated the particles are) and the Y-axis shows glucose concentration (g/l).

FIG. 4 show the shape of the particles. A shape near 0 is a very long very thin object and a shape of 1 is a perfect circle. As shown in FIG. 4, the highest enzymatic availability is observed at a form factor of about 0.645.

Example 4

FIG. 1 shows an exemplary system for the preparation of a hydrolysate containing sugar from a cellulosic starting material according to the present invention. The system comprises a pretreatment arrangement (1) for the preparation of a slurry comprising cellulosic particles from a cellulosic starting material. Said pretreatment arrangement (1) comprises an inlet (2) and an outlet (3). The system further comprises an enzymatic hydrolysis reactor (4) for saccharification of the pretreated slurry. The enzymatic hydrolysis reactor (4) comprises an inlet (5) connected to the outlet of the pretreatment arrangement (3). The system further comprises an analyzing unit (6) comprising a sample inlet valve (7) a sample dilution tank (8), a circulation pump (9), a flow cell (10), a light source (11) capable of emitting light in the visible spectrum, a camera lens (12) and a digital camera (13) capable of capturing an image of in the visible spectrum; and an image processing device (14) capable of processing data received from the digital camera (13) such that information of size, shape and/or degree of darkness of the cellulosic particles can be obtained. The system is further comprising a slurry sample outlet (15) provided on the connection between the outlet of the pretreatment arrangement (3) and the inlet of the enzymatic hydrolysis reactor (5). Lignocellulosic biomass is introduced into the pretreatment arrangement (1) through the inlet (2) of the pretreatment arrangement (1) and pretreated slurry exits the pretreatment arrangement (1) through the outlet (3). A sample of pretreated slurry is diverted to the analyzing unit (6) via the slurry sample outlet (15). The sample enters the sample dilution tank (8) via the sample inlet valve (7) where it is diluted to proper consistency. The sample is thereafter pumped in to the flow cell (10) by means of the circulation pump (9). In the flow cell about 2000 pictures is captured by the digital camera (13) and digital information is sent to the image processing device (14) for processing of the data using software adapted to execute image analysis. The processed data gives information of the enzymatic availability of the pretreated biomass and can be used for feed-back control of the pretreatment process and/or for feed-forward control of the enzymatic hydrolysis process. The analyzed and/or excess sample can either be discarded or returned to the enzymatic hydrolysis process through a sample return inlet (16).

The invention claimed is:
1. A method of producing a hydrolysate containing sugar from a lignocellulosic biomass, comprising the steps of:
   a) pretreating the lignocellulosic biomass in a pretreatment process to form a slurry comprising cellulosic particles;
   b) saccharification of the slurry obtained in step a) in the presence of hydrolytic enzymes in an enzymatic hydrolysis process to obtain a hydrolysate containing sugar;
   c) analyzing cellulosic particles present in the slurry obtained in step a) and/or cellulosic particles present in the enzymatic hydrolysis process during step b) using an image analysis method to obtain a data set; and
   d) controlling at least one process parameter of the pretreatment process in step a) and/or enzymatic hydrolysis process in step b) in response to the data set obtained in step c); wherein the image analysis in step c) is a visible spectrum image analysis.
2. Method according to claim 1, wherein the process parameter controlled in step d) is selected from:
   a pH-value of the pretreatment process;

a residence time of the cellulosic material in the pretreatment process;
a temperature of the pretreatment process;
a pressure of the pretreatment process;
an amount of hydrolytic enzymes added in the enzymatic hydrolysis process;
a residence time of the cellulosic material in the enzymatic hydrolysis process;
a biomass composition of the lignocellulosic biomass pretreated in step a); and
a degree of disintegration of the biomass prior to the pretreatment in step a).

3. Method according to claim 1, wherein the step c) is an online analysis and the method further includes a step of diverting a sample comprising cellulosic particles after the pretreatment process in step a) but prior to the enzymatic hydrolysis process in step b) and wherein the analyzing of cellulosic particles in step c) is performed on the said diverted sample.

4. Method according to claim 1, wherein the step c) is an online analysis and the method further includes a step of diverting a sample comprising cellulosic particles from the enzymatic hydrolysis process in step b) and wherein the analyzing of cellulosic particles in step c) is performed on the said diverted sample.

5. Method according to claim 1, wherein step c) includes taking a digital image in the visible range and processing the image using an algorithm such that the data set is obtained.

6. Method according to claim 1, wherein step c) further includes determining a size, a shape, and/or a degree of darkness of the cellulosic particles based on the obtained data set.

7. Method according to claim 6, wherein the size and/or degree of darkness of cellulosic particles is determined in step c) and compared to a reference value and if the size is larger than the reference value and/or if the degree of darkness of the cellulose particles is lower than the reference value, at least one of the following process adjustments are performed:
increase of the severity of the pretreatment process;
increase of the efficiency of the enzymatic hydrolysis process; and
increase a degree of disintegration of the biomass prior to the pretreatment in step a).

8. Method according to claim 6, wherein the size and/or degree of darkness of cellulosic particles is determined in step c) and compared to a reference value and if the size is smaller than the reference value and/or if the degree of darkness of the cellulose particles is higher than the reference value, at least one of the following process adjustments are performed:
decrease of the severity of the pretreatment process;
decrease of the efficiency of the enzymatic hydrolysis process; and
decrease a degree of disintegration of the biomass prior to the pretreatment in step a).

9. Method according to claim 7, wherein the severity of the pretreatment process is increased by increasing a pressure, temperature and/or residence time in the pretreatment and/or by changing a pH value in the pretreatment process.

10. Method according to claim 8, wherein the severity of the pretreatment is decreased by decreasing a pressure, temperature and/or residence time in the pretreatment and/or by changing a pH value in the pretreatment process.

11. Method according to claim 7, wherein the efficiency of the enzymatic hydrolysis is increased by increasing the amount of hydrolytic enzyme in the enzymatic hydrolysis process and/or by increasing a residence time of the cellulosic material in the enzymatic hydrolysis process.

12. Method according to claims 8, wherein the efficiency of the enzymatic hydrolysis is decreased by decreasing the amount of hydrolytic enzyme in the enzymatic hydrolysis process and/or by decreasing a residence time of the cellulosic material in the enzymatic hydrolysis process.

13. System for the preparation of a hydrolysate containing sugar from a cellulosic starting material, wherein the system comprises:
i) a pretreatment arrangement for the preparation of a slurry comprising cellulosic particles from a cellulosic starting material, wherein the pretreatment arrangement comprises an inlet and an outlet;
ii) an enzymatic hydrolysis reactor for saccharification of the slurry from the pretreatment comprising an inlet connected to the outlet of the pretreatment arrangement;
iii) an image capturing device comprising a light source capable of emitting light in the visible spectrum, a camera lens and a digital camera capable of capturing an image in the visible spectrum;
iv) an image processing device connected to the image capturing device and capable of processing data received from the image capturing device such that information about a size, shape and/or degree of darkness of the cellulosic particles can be obtained;
and wherein the image capturing device is arranged to capture images of cellulosic particles present:
in the slurry at a position in the connection between the outlet of the pretreatment arrangement and the inlet of the enzymatic hydrolysis arrangement;
in a slurry sample diverted from a position in the connection between the outlet of the pretreatment arrangement and the inlet of the enzymatic hydrolysis arrangement;
in the enzymatic hydrolysis reactor; and/or
in a sample diverted from the enzymatic hydrolysis reactor.

14. System according to claim 13, wherein the system further comprises a slurry sample outlet provided on the connection between the outlet of the pretreatment arrangement and the inlet of the enzymatic hydrolysis reactor, wherein the image capturing device is arranged to capture images of cellulose particles within a slurry sample diverted through the slurry sample outlet.

15. System according to claim 13, wherein the system further comprises a hydrolysate sample outlet provided on the enzymatic hydrolysis reactor, wherein the image capturing device is arranged to capture images of cellulose particles within a hydrolysate sample diverted through the hydrolysate sample outlet.

* * * * *

UNITED STATES PATENT AND TRADEMARK OFFICE
CERTIFICATE OF CORRECTION

PATENT NO. : 9,580,763 B2
APPLICATION NO. : 14/759108
DATED : February 28, 2017
INVENTOR(S) : Wallberg et al.

It is certified that error appears in the above-identified patent and that said Letters Patent is hereby corrected as shown below:

On the Title Page (30) Foreign Application Priority Data:
Please correct "(EP) ................13152377" to read -- (EP) ................13152377.1 --

In the Specification

Column 3, Line 23: Please correct "present invention" to read -- present invention. --

Column 6, Line 35: Please correct "in step a)" to read -- in step a). --

In the Claims

Column 16, Line 10, Claim 12: Please correct "according to claims 8," to read -- according to claim 8, --

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*